United States Patent [19]

Weinert

[11] Patent Number: 4,486,404

[45] Date of Patent: Dec. 4, 1984

[54] TOOTH AND MOUTH CARE AGENTS

[75] Inventor: Wolfgang Weinert, Bad Schwalbach, Fed. Rep. of Germany

[73] Assignee: Blendax-Werke R. Schneider GmbH & Co., Rheinallee, Fed. Rep. of Germany

[21] Appl. No.: 547,417

[22] Filed: Oct. 31, 1983

[30] Foreign Application Priority Data

Nov. 6, 1982 [DE] Fed. Rep. of Germany ....... 3241017

[51] Int. Cl.$^3$ .......................... A61K 7/22; A61K 7/26
[52] U.S. Cl. ........................................ 424/54; 424/58; 424/195
[58] Field of Search ............................ 424/54, 58, 195

[56] References Cited

U.S. PATENT DOCUMENTS

| | | | |
|---|---|---|---|
| 2,526,614 | 10/1950 | Butterfield | 424/54 |
| 2,542,518 | 2/1951 | Henschel | 424/54 |
| 2,542,886 | 2/1951 | Wach | 424/54 |
| 2,549,759 | 4/1951 | Goodfriend | 424/54 |
| 2,588,324 | 3/1952 | Lewis et al. | 424/54 |
| 2,588,992 | 3/1952 | Schlaeger | 424/54 |
| 2,601,238 | 6/1952 | Bell | 424/54 |
| 2,647,073 | 7/1953 | Singer | 424/54 |
| 3,170,916 | 2/1965 | Dziengel | 424/58 |

FOREIGN PATENT DOCUMENTS 5782307   5/1982   Japan ..................... 424/58

OTHER PUBLICATIONS

Journal of Periodontology, vol. 37, pp. 20–33 (1966).
Hager's Handbook of Pharmaceutical Practice, 4th Ed., vol. II, Published by Springer, pp. 1110–1115 (1969).

*Primary Examiner*—Shep K. Rose
*Attorney, Agent, or Firm*—Connolly and Hutz

[57] ABSTRACT

A tooth and mouth care composition is improved by a synergistic mixture of urea and horse chestnut extract.

4 Claims, No Drawings

TOOTH AND MOUTH CARE AGENTS

The present invention concerns a new agent for care of the teeth and the mouth, the effect of which maintains the health of the gums and particularly diminishes gingivitis and prevents or decreases the bleeding of the gums.

Tooth and mouth care agents with similar purposes have long been known and are also commercially available.

For these toothpastes, different active agents have been suggested. A recognized substance in this respect is urea, which has also been introduced into the practice. The description of this substance not only states that it has a caries-prophylactic effect and prevents the formation of dental calculus (cf Journal of Periodontology, Vol. 37, (1966, pp 20–33)), but it also has a keratinizing effect, i.e., when present in sufficient concentration in agents for tooth and mouth care, it strengthens the gums, which can be demonstrated by a significant increase in the keratinization-index.

It has now been found that the effect on the gums of tooth and mouth care agents containing urea can be further increased, particularly in respect to prevention of bleeding of the gums, if horse-chestnut extract is added to these agents, preferably in a quantity of between approx. 0.1% and 1% by weight, calculated on the total composition.

The use of horse-chestnut extract in tooth and mouth care agents is also previously known and described e.g. in the German Accepted Specification No. 1 139 609.

However, toothpastes, containing horse-chestnut extracts in the tooth and mouth care have not been used practically. Thus, it was highly surprising and not to be expected, that by means of a combination of the two effective agents urea and horse-chestnut extract in a tooth and mouth care agent, particularly in a toothpaste, a synergistic increase of the effect would be obtained in respect to the treatment of the gums.

A particularly favorable effect was obtained when a toothpaste, containing at least 5% by weight urea, preferably 8% by weight, with approximately 0.1% to approx. 1%, preferably approx. 0.5% by weight horse-chestnut extract in relation to the total composition, was subjected to a clinical investigation.

Within the scope of the present invention, horse-chestnut extract is understood as the alcoholic and aqueous-alcoholic extract of the peeled seeds of *Aesculus hippocastanum*.

It is advantageous to remove the tannins and proteins contained in the alcoholic or aqueous-alcoholic extracts before, although this is not absolutely necessary for obtaining the effect according to the invention.

The horse-chestnut extract applied is preferably a dry extract standardized to an aescin content between approx. 17% and 19%, but a liquid extract can definitely also be used, whereby the preferred quantity must then be correspondingly calculated to the standardized quantity of the dry extract.

A description of horse-chestnut extract and its pharmacological properties can be found in "Hagers Handbuch der pharmazeutischen Praxis" (Hager's Handbook of Pharmaceutical Practice), 4th edition, Vol. II (Publ. By Springer, 1969), pp 1110–1115. As already stated, the preferred quantity of horse-chestnut extract in the tooth and mouth care agents according to the invention amounts to approx. 0.1% to 1.0% by weight of the total composition. If higher proportions than 1% are used, there is a risk for irritation of the mucous membranes; an optimum dosage is between approx. 0.5% and 0.6% by weight, e.g. 0.55% by weight of the total composition.

The proportion of urea in the tooth and mouth care agents according to the invention is at least 5% by weight of the total composition; a particularly favorable effect has been found with a combination of 5%–8% urea by weight of horse-chestnut extract. Generally, the urea content does not exceed 15% by weight, preferably 10% by weight, related to the total composition.

The preferred application is in a tooth-paste, although in principle, any application of a tooth and mouth care agent containing urea and horse-chestnut extract can be used, such as, for instance, mouthwashes, sprays, or tooth powders.

A toothpaste may be opaque or may be transparent, containing a suitable polishing agent with a refraction index corresponding to the refraction index of the carrier material.

A particularly appropriate toothpaste is described in the Luxembourgian Pat. No. 82,933; it contains as polishing agent calcium carbonate and at least 5% by weight urea, approx. 0.5% to 1.6% by weight of an alkaline salt of a higher fatty acid with about 12 to about 16 carbon atoms, it contains basically no synthetic tensides, and has a pH of at least 7.5 in the alkaline range, preferably between 7.5 and 9.5.

However, it is also possible to use toothpastes based on other substances, containing polishing agents such as e.g. alkali aluminum silicates, particularly those of the Zeolite Type A, described in European Pat. Nos. 2690 and 3023, various calcium phosphates such as dicalcium orthophosphate in the form of its dihydrate or water-free, tricalcium phosphate, calcium pyrophosphate, insoluble alkali metaphosphate, alumina, or alumina trihydrate, silica in various modifications, such as silica xerogels, hydrogels, or precipitated silicas, or synthetic plastics materials in a powder form.

Naturally, polishing mixtures of the above mentioned substances may be used, e.g. a mixture of calcium carbonate and synthetic Zeolite A in a ratio of approx. 1:1.

The proportion of polishing agent in the toothpastes according to the invention is preferably between approx. 20% and 60% by weight of the total composition.

As already indicated, a preferred embodiment of the present invention is to include the synergistic combination of urea and horse-chestnut extract in such toothpastes which contain only a small or no proportion of synthetic surface-active substances but may rather contain alkali salts or higher fatty acids, e.g. those of lauric acid, myristic acid, parmitic acid, stearic acid, or mixtures of these, e.g. coconut fatty acids or tallow fatty acids. Such salts of higher fatty acids are preferably present in a quantity of between approx. 0.5% and 1.5% by weight of the total composition.

However, it is also possible to use the surface-active compounds usually included in toothpastes in quantities of up to approx. 2% by weight of the total composition, optionally in admixture with the above mentioned salts of fatty acids. Such synthetic surface-active substances are e.g. alkyl sulphates, alkyl ether sulphates, olefin sulphonates, sodium lauryl sarcosinate or ampholytic, non-ionic or cation-active compounds.

A summary of the compounds that may be included in toothpastes as well of other substances commonly used in the production of tooth-care agents and the production methods for these can be found in the monography of M. S. Balsam and E. Sagarin, "Cosmetics—Science and Technology", 2nd ed., Vol. I, pp 423-533 (1972), to which reference is made.

The same applies to the moisture-retaining agents commonly used in toothpastes in a proportion between approx. 10% and approx. 35% by weight, e.g. glycerol, diols such as 1,4-butanediol or 1,2-propanediol, or sugar alcohols such as sorbitol, mannitol and xylitol, and polyglycols with low molecular weights, as well as to the thickeners, of which the proportion in toothpastes amounts to between approx. 0.25% and approx. 5% by weight of the total composition.

Preferred thickeners are carboxymethyl cellulose and its alkali salts, particularly sodium carboxymethyl cellulose, hydroxyalkyl celluloses such as hydroxymethyl cellulose and hydroxyethyl cellulose, methyl cellulose, plant gums such as tragacanth, caraya gum, guar gum, xanthan gum, and Irish moss, synthetic polyelectrolytes such as alkali salts of polyacrylic acids, as well as inorganic thickeners, e.g. colloidal magnesium aluminum silicate or colloidal silica.

Naturally, other substances may also be used in the tooth and mouth-care agents according to the invention, particularly such as the known caries-prophylactic fluorides, preferably in such a quantity that the concentration of pure fluorine in the preparation amounts to approx. 0.05% to approx. 1% by weight, preferably 0.1% to 0.5% by weight of the preparation.

Suitable fluorine compounds are particularly the various salts of monofluorophosphoric acid, particularly sodium, potassium, lithium, calcium and aluminum mono- and difluorophosphates, as well as the various fluorides containing fluorine in ionically bound form, particularly alkali fluorides such as sodium, lithium, potassium and ammonium fluoride, stannous fluoride, manganese fluoride, copper fluoride, zirconium fluoride, and aluminum fluoride, as well as mixtures or addition products of these fluorides mutually or with other fluorine compounds, e.g. alkali manganese fluoride.

Organic fluorine compounds can also be successfully used, particularly the known addition products of long-chain amines or amino acids and hydrogen fluoride, monoethanolamine hydrofluoride, or monoethyl triethyl ammonium fluoride.

Additional substances which may be added to the tooth and mouth care preparations according to the invention are substances that prevent dental plaque formation, e.g. bisguanides known under the trade names "Chlorhexidine" or "Alexidine", 1,6-di-4'-(chorophenyl diguanido) hexane or 1,6-di-(2-ethylhexyl diguanido)hexane or their preferably water-soluble salts; compounds to prevent the formation of dental calculus, such as hydroxyethane-1,1-diphosphonic acid or alkylene (tetramethylene phosphonic acids) and their water-soluble salts, allantoin, azulen, etc.

In the following, some examples will be given which characterize the nature of the present invention and the advantageous effects thereof:

EXAMPLE 1

| Opaque Toothpaste | % by weight |
| --- | --- |
| Methyl hydroxyethyl cellulose | 1.00 |
| Calcium carbonate | 42.00 |
| Urea | 8.00 |
| Allantoin | 0.30 |

-continued

| Opaque Toothpaste | % by weight |
| --- | --- |
| Sodium laurate | 0.65 |
| Sodium benzoate | 0.30 |
| Methyl p-hydroxybenzoate | 0.15 |
| Saccharin sodium | 0.05 |
| Sorbitol, 70% | 8.00 |
| Horse chestnut extract (standardized to 18% aescin) | 0.60 |
| Colloidal silica | 0.35 |
| Flavour composition | 1.00 |
| Water | 37.60 |

EXAMPLE 2

| Opaque Toothpaste | % by weight |
| --- | --- |
| Urea | 6.00 |
| Sodium monofluorophosphate | 0.75 |
| Allantoin | 0.10 |
| Sodium stearate/laurate (1:1) | 0.70 |
| Sodium benzoate | 0.25 |
| Calcium carbonate | 40.00 |
| Methyl p-hydroxybenzoate | 0.15 |
| Sodium cyclamate | 0.10 |
| Calcium silicate | 0.50 |
| Hydroxyethyl cellulose | 1.10 |
| Sorbitol, 70% | 9.00 |
| Flavour composition | 1.00 |
| Horse chestnut extract | 0.55 |
| Water | 39.80 |

EXAMPLE 3

| Opaque Toothpaste | % by weight |
| --- | --- |
| Calcium carbonate | 22.50 |
| Synthetic Zeolite A (according to European Pat. No. 3023; $Na_{12}(AlO_2)_{12}(SiO_2)_{12}\cdot 27H_2O$) | 16.50 |
| Sorbitol, 70% | 7.50 |
| Glycerol | 3.50 |
| Carboxymethyl cellulose | 1.20 |
| Benzoic acid | 0.30 |
| Methyl p-hydroxybenzoate | 0.10 |
| Saccharin sodium | 0.05 |
| Sodium monofluorophosphate | 1.25 |
| Colloidal silica | 0.20 |
| Urea | 10.00 |
| Horse chestnut extract | 0.80 |
| Flavour mixture | 1.00 |
| Sodium lauryl sulphate, 86% | 1.20 |
| Water | 33.90 |

EXAMPLE 4

| Transparent Toothpaste | % by weight |
| --- | --- |
| Carboxymethyl cellulose | 0.50 |
| Sodium benzoate | 0.15 |
| Polyethylene glycol 400 | 5.00 |
| Glycerol | 45.00 |
| Urea | 7.50 |
| Horse chestnut extract | 0.55 |
| Allantoin | 0.15 |
| Guajazulene | 0.05 |
| Saccharin sodium | 0.07 |
| Sodium lauroyl sarcosinate | 1.10 |
| Phenyl salicylate | 0.10 |
| Flavour composition | 1.00 |
| 10% blue dye mixture | 0.03 |
| Dehydrated silica gel (surface 290 $m^2/g$; average particle diameter 6 $\mu m$) | 20.00 |

-continued

| Transparent Toothpaste | % by weight |
| --- | --- |
| Water | 18.80 |

EXAMPLE 5

| Opaque Toothpaste | % by weight |
| --- | --- |
| Chlorhexidine digluconate | 0.10 |
| Urea | 8.00 |
| Horse chestnut extract | 0.65 |
| Allantoin | 0.20 |
| Sodium fluoride | 0.30 |
| Alumina trihydrate | 25.00 |
| Zeolite A | 15.00 |
| (according to European Pat. No. 3023; $Na_{12}(AlO_2)_{12}(SiO_2)_{12}\cdot 27H_2O$) | |
| Medical soap (German Pharmacopoe No. 6) | 0.70 |
| Sodium sulphoricinoleate | 0.30 |
| Hydroxyethyl cellulose | 1.05 |
| Propyl p-hydroxybenzoate | 0.15 |
| Methyl p-hydroxybenzoate | 0.15 |
| Sodium benzoate | 0.15 |
| Saccharin sodium | 0.05 |
| Glycerol | 8.50 |
| Sorbitol, 70% | 7.50 |
| Flavour composition | 1.20 |
| Water | 31.00 |

Clinical Investigation Demonstrating the Synergistic Effect of the Combination According to the Invention Sixty adult subjects were divided into 3 groups of 20 persons each.

For each subject, the sulcus bleeding index and the sulcus fluid flow rate were determined; both indices show the health status of the gums.

Thereafter, each one of the groups was given a toothpaste with the designation A, B, or C, to be used twice daily, identical toothbrushes were given to all subjects.

After 30 days, the subjects were examined again, and the above mentioned indices were determined.

The following result was obtained:

| | Paste A | | Paste B | | Paste C | |
| --- | --- | --- | --- | --- | --- | --- |
| Day | 0 | 30 | 0 | 30 | 0 | 30 |
| Sulcus fluid flow rate | 3.20 ± 0.22 | 3.34 ± 0.23 | 3.22 ± 0.23 | 2.02 ± 0.56 | 3.25 ± 1.07 | 3.07 ± 0.27 |
| Sulcus bleeding index | 1.88 ± 0.33 | 2.44 ± 0.65 | 1.90 ± 0.62 | 1.35 ± 0.36 | 1.89 ± 0.63 | 1.86 ± 0.60 |

Paste B was a toothpaste according to Example 1; Paste A was a toothpaste according to Example 1 but without urea, whereby the weight was balanced by increasing the water contents; Paste C was a toothpaste according to Example 1, but without horse chestnut extract, whereby the weight was also balanced by increasing the water contents.

As can be clearly seen from the table, a significant, surprising decrease of the relevant indices for tendency to bleeding of the gums is obtained with the toothpaste according to the invention, as per Example 1, compared to the toothpastes corresponding to the state of the art and merely containing the single components of the synergistic mixture according to the invention.

What is claimed is:

1. A composition for tooth and mouth care containing at least 5% by weight urea and additionally 0.1 to 1% by weight horse chestnut extract.

2. The tooth and mouth care composition according to claim 1 containing 0.5% to 0.6% by weight of horse chestnut extract, related to the total composition.

3. The tooth and mouth care composition according to claim 1 in the form of an aqueous based toothpaste composition having a pH above 7.5, containing calcium carbonate as polishing agent, 5% to 15% by weight urea, 0.5% to 1% by weight of an alkali metal salt of a fatty acid having 12 to 22 carbon atoms and 0.1 to 1% by weight horse chestnut extract.

4. The tooth and mouth care composition according to claim 3 containing 0.5% to 0.6% by weight of horse chestnut extract, related to the total composition.

* * * * *